(12) United States Patent
Bilu et al.

(10) Patent No.: US 10,639,484 B2
(45) Date of Patent: May 5, 2020

(54) IMPLANTABLE ELECTRONIC DEVICE EMPLOYING COATED LEAD RETAINING SETSCREWS

(71) Applicant: PACESETTER, INC., Sylmar, CA (US)

(72) Inventors: Avi Bilu, Pasadena, CA (US); Daniel Choi, Saratoga, CA (US); Asghar Dadashian, Porter Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 84 days.

(21) Appl. No.: 15/788,239

(22) Filed: Oct. 19, 2017

(65) Prior Publication Data
US 2019/0117981 A1    Apr. 25, 2019

(51) Int. Cl.
| | | |
|---|---|---|
| *A61N 1/375* | (2006.01) |
| *B05D 1/00* | (2006.01) |
| *B05D 3/10* | (2006.01) |

(52) U.S. Cl.
CPC ............ *A61N 1/3752* (2013.01); *B05D 1/60* (2013.01); *B05D 3/102* (2013.01); *B05D 2258/00* (2013.01)

(58) Field of Classification Search
CPC . A61N 1/05; A61N 1/37; A61N 1/375; A61N 1/3752; A61N 1/3754; A61N 1/3758; B05D 1/60; B05D 1/62
See application file for complete search history.

(56) References Cited

U.S. PATENT DOCUMENTS

| | | | | |
|---|---|---|---|---|
| 4,764,132 A * | 8/1988 | Stutz, Jr. | ............... | A61N 1/3752 439/810 |
| 4,860,750 A * | 8/1989 | Frey | ...................... | A61N 1/3752 607/37 |
| 5,509,928 A * | 4/1996 | Acken | .................. | A61N 1/3752 439/519 |
| 5,529,579 A * | 6/1996 | Alt | ......................... | A61N 1/375 607/36 |
| 5,662,692 A * | 9/1997 | Paspa | ................... | A61N 1/3752 607/37 |
| 6,032,677 A * | 3/2000 | Blechman | ............... | A61B 17/86 128/899 |
| 6,984,145 B1 * | 1/2006 | Lim | ..................... | A61N 1/3752 439/462 |
| 7,016,734 B2 * | 3/2006 | Persuitti | ............... | A61N 1/3752 403/362 |
| 7,133,722 B2 * | 11/2006 | Hansen | ................. | A61N 1/3752 607/37 |
| 7,155,283 B2 * | 12/2006 | Ries | ..................... | A61N 1/3752 607/37 |
| 7,210,968 B1 * | 5/2007 | Gister | ...................... | H01R 4/44 439/668 |
| 7,231,253 B2 * | 6/2007 | Tidemand | .............. | A61N 1/375 607/37 |

(Continued)

*Primary Examiner* — Christopher A Flory
(74) *Attorney, Agent, or Firm* — Polsinelli PC (57) ABSTRACT

Disclosed herein is an implantable electronic device for use with implantable medical leads. The implantable medical leads are retained within the implantable electronic device with coated setscrews and, in particular, setscrews having a vapor-deposited coating, such as parylene. The coated setscrews have improved thread locking capabilities that resist unscrewing once tightened and, as a result, improve retention of implantable leads within the implantable electronic device.

16 Claims, 7 Drawing Sheets

(56) References Cited

U.S. PATENT DOCUMENTS

| | | | | |
|---|---|---|---|---|
| 7,303,422 B2* | 12/2007 | Hoffer | | H01R 13/5224 439/359 |
| 7,308,312 B1* | 12/2007 | Lim | | A61N 1/3752 439/362 |
| 7,308,313 B1* | 12/2007 | Lim | | A61N 1/3752 439/362 |
| 8,032,221 B2* | 10/2011 | Wengreen | | A61N 1/3752 607/37 |
| 8,190,260 B2* | 5/2012 | Ries | | A61N 1/3752 607/37 |
| 9,095,391 B2* | 8/2015 | McKinley | | A61B 17/866 |
| 2002/0107547 A1* | 8/2002 | Erlinger | | A61N 1/3956 607/5 |
| 2002/0161369 A1* | 10/2002 | Bramlet | | A61B 17/7225 606/67 |
| 2004/0068215 A1* | 4/2004 | Adelson | | A61F 5/0123 602/26 |
| 2004/0106959 A1* | 6/2004 | Schmidt | | A61N 1/056 607/11 |
| 2004/0122481 A1* | 6/2004 | Tidemand | | A61N 1/375 607/37 |
| 2004/0143314 A1* | 7/2004 | Sommer | | A61M 25/0082 607/120 |
| 2004/0147963 A1* | 7/2004 | Sommer | | A61M 25/0082 607/3 |
| 2005/0118887 A1* | 6/2005 | Hoffer | | H01R 13/5224 439/810 |
| 2005/0131481 A1* | 6/2005 | Ries | | A61N 1/3752 607/36 |
| 2005/0131483 A1* | 6/2005 | Zhao | | A61N 1/3752 607/36 |
| 2007/0112353 A1* | 5/2007 | Berckmans, III | | A61B 17/866 606/86 A |
| 2007/0232936 A1* | 10/2007 | Mann | | A61B 5/0215 600/486 |
| 2007/0244402 A1* | 10/2007 | Brockway | | A61B 5/046 600/509 |
| 2007/0270835 A1* | 11/2007 | Wisnewski | | A61B 17/7032 606/86 A |
| 2008/0177330 A1* | 7/2008 | Ralph | | A61B 17/8038 606/290 |
| 2008/0306554 A1* | 12/2008 | McKinley | | A61B 17/866 606/301 |
| 2009/0112207 A1* | 4/2009 | Walker | | A61B 17/7016 606/57 |
| 2009/0263641 A1* | 10/2009 | Martin, III | | B05D 1/60 428/221 |
| 2010/0016918 A1* | 1/2010 | Mann | | A61N 1/025 607/23 |
| 2010/0082072 A1* | 4/2010 | Sybert | | A61B 17/68 606/326 |
| 2010/0179562 A1* | 7/2010 | Linker | | A61N 1/0551 606/129 |
| 2010/0249869 A1* | 9/2010 | Ries | | A61N 1/3752 607/37 |
| 2010/0249870 A1* | 9/2010 | Wengreen | | A61N 1/3752 607/37 |
| 2011/0190833 A1* | 8/2011 | Ries | | A61N 1/375 607/2 |
| 2013/0126092 A1* | 5/2013 | Sexton | | H01J 37/3288 156/345.1 |
| 2014/0182772 A1* | 7/2014 | Wrobel | | C08F 265/02 156/91 |
| 2014/0214129 A1* | 7/2014 | Waataja | | A61N 1/36007 607/59 |
| 2014/0228905 A1* | 8/2014 | Bolea | | A61N 1/0556 607/42 |
| 2015/0018923 A1* | 1/2015 | Nolan | | A61N 1/3752 607/122 |
| 2015/0157851 A1* | 6/2015 | Sefkow | | A61N 1/0534 607/116 |
| 2016/0129260 A1* | 5/2016 | Mann | | A61B 5/0215 607/23 |
| 2016/0136436 A1* | 5/2016 | Nolan | | A61N 1/3752 607/122 |
| 2017/0268844 A1* | 9/2017 | Smith | | F41A 21/487 |
| 2017/0312499 A1* | 11/2017 | Linker | | A61N 1/0551 |
| 2018/0091089 A1* | 3/2018 | Lange | | H02S 20/32 |
| 2018/0159248 A1* | 6/2018 | Ruland | | H01R 4/302 |
| 2018/0271568 A1* | 9/2018 | Pool | | A61B 17/1725 |

* cited by examiner

IMPLANTABLE ELECTRONIC DEVICE EMPLOYING COATED LEAD RETAINING SETSCREWS

FIELD OF THE INVENTION

Aspects of the present invention relate to medical apparatus and methods. More specifically, the present invention relates to an implantable electronic device including coated setscrews for retaining proximal ends of implantable medical leads within a header of the implantable electronic device.

BACKGROUND OF THE INVENTION

Implantable electronic devices (EDs) include implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems. These IPGs commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

A header of an IPG encloses the connector assembly, which has many internal electrically conductive components such as, for example, wires, ribbon, antennas, blocks, rings, etc. The connector assembly further includes one or more connector blocks into which terminal ends of leads may be inserted. In certain IPGs, the connector blocks or adjacent structures may include setscrews that may be tightened after insertion of a terminal lead end to fix the terminal lead end. However, after tightening, such setscrews may become loosened by movement of the patient. Accordingly, there is a need in the art for setscrews and IPGs including setscrews that more reliably retain terminal lead ends within the header.

BRIEF SUMMARY OF THE INVENTION

Disclosed herein is an implantable electronic device for use with an implantable medical lead having a proximal lead end. The implantable electronic device includes a housing and a header connector assembly coupled to the housing, the header connector assembly defining a threaded setscrew hole and including a connector assembly adjacent the threaded setscrew hole. The connector assembly is adapted to receive the proximal lead end of the implantable medical lead. The implantable electronic device further includes a setscrew threadedly movable within the threaded setscrew hole to retain the proximal lead end within the connector assembly. The setscrew includes a threaded body and a vapor-deposited coating disposed on a portion of the threaded body.

In one implementation, the vapor-deposited coating is a poly(p-xylelene) polymer coating and, in a more specific implementation, is a parylene coating. In certain implementations, the thickness of the coating may be from and including 0.0001 inches to and including 0.005 inches.

In certain implementations, the setscrew may be formed from a substrate such as one of titanium and stainless steel. The setscrew may also include a passivated outer layer onto which the vapor-deposited coating is applied.

In other implementations, the threaded body of the setscrew may define a socket shaped to receive a tool for rotating the setscrew within the threaded setscrew bore. In such implementations, the vapor-deposited coating may be excluded from the socket.

In certain implementations, the setscrew may include a thread having a pitch from and including 0.0125 inches to and including 0.2222 inches and a pitch diameter from and including 0.06 inches in to and including 2.0 inches. The coating and setscrew may also be designed such that rotating the setscrew within the threaded setscrew bore requires from and including 0.20 ounce-inches to and including 2.0 ounce-inches of torque.

In another embodiment of the present disclosure, a method of manufacturing an implantable electronic device including a header that further includes a connector assembly and a threaded setscrew bore adjacent the connector assembly is provided. The method includes producing a coated setscrew by applying a vapor-deposited coating to a setscrew substrate, and at least one of providing the coated setscrew with the implantable electronic device or threadedly engaging the coated setscrew within the threaded setscrew bore.

In one implementation, the vapor-deposited coating is a poly(p-xylelene) polymer coating and, in a more specific implementation, is a parylene coating. In certain implementations, the thickness of the coating may be from and including 0.0001 inches to and including 0.005 inches.

The method may further include applying a primer to the setscrew before applying the vapor-deposited coating. In certain implementations, for example, the primer may include silane. The setscrew may also be passivated prior to applying the vapor-deposited coating.

In still other implementations, the method may include masking a portion of the setscrew such that the vapor-deposited coating is not applied to the masked portion of the setscrew. Such masking may include, among other things, applying at least one of a masking dot, tape, a contact pad, and a masking solution to the portion of the setscrew.

In certain implementations, the setscrew includes a socket and the method further comprises supporting the setscrew on a fixture shaped to be inserted into the socket such that the fixture prevents application of the vapor-deposited coating to the socket.

DETAILED DESCRIPTION

Implementations of the present disclosure involve an implantable electronic device (IED) such as an implantable pulse generator (IPG). The IPG administers electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one lead connector receiving bore or receptacle that includes electrical contacts of the connector assembly that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

Setscrews may be used in the headers to secure leads in place within corresponding lead bores or connector blocks. Following insertion of leads into the header and securing of the leads using the setscrews, patient movement may eventually cause the setscrews to loosen, reducing the quality of the connection between the lead and the connector blocks and, in extreme circumstances, causing the lead to be become dislodged from the header. To reduce the likelihood of such loosening, setscrews may be coated or treated with a medical adhesive or similar solution. While such solutions generally provide thread-locking capability, the process of applying the solution to the setscrews may be time-consuming and highly dependent on the skill of the individual applying the solution to obtain even coverage. For example, many such solutions require extensive cleaning of the setscrews, manual application of the solution, and an extended curing time that may, in some instances, exceed 12 hours.

Conventional adhesive solutions may also be free flowing, compounding the difficulty of applying a uniform layer of the adhesive solution over a given setscrew. For example, flowing of the adhesive solution prior to curing may result in pooling or similar buildup in certain areas of the setscrew. Such buildup may result in uneven thread locking of the setscrew and breaking off of the built up portion of the adhesive solution. If buildup occurs on the threaded portion of the setscrew, the setscrew may seize within the header, preventing proper installation or removal of the setscrew and increasing the likelihood that the socket of the setscrew may become stripped. Buildup may also occur in the socket, obstructing insertion of tools for rotating the setscrew.

In addition to issues caused by inconsistent application of conventional adhesive solutions, many conventional adhesive solutions are prone to wear and cracking after application. Such wear may result from vibration caused by handling during transportation and/or general movement of the patient following implantation of an IPG in which a coated setscrew is mounted. As the adhesive coating wears and breaks away, the setscrew may loosen within the IPG header and may require retightening or even replacement. To do so, a physician must generally use a torque driver or similar tool to either tighten the existing screw or back the existing screw out and screw in a new screw. This unnecessary insertion of the torque driver may damage a septum covering the setscrew hole and providing a seal between the setscrew hole and the body of the IPG. If sufficiently damaged, the seal provided by the septum may be compromised such that highly conductive bodily fluids may enter into the lead bore, resulting in malfunction or failure of the IPG.

To address the foregoing issues, IPGs in accordance with the present disclosure include setscrews coated with a vapor deposited polymer. In certain implementations, the vapor deposited is a poly(p-xylelene) polymer, such as parylene. While such polymers have been used to coat other implantable medical equipment, such conventional uses are limited to providing moisture or dielectric barriers or lubricating equipment surfaces. The particular use of poly(p-xylelene) polymers as a biocompatible thread locking compound has not been contemplated and is contrary to the lubrication applications for which poly(p-xylelene) polymers are typically used.

The proposed setscrew coating eliminates many of the foregoing problems associated with conventional adhesive solutions. The vapor deposition process generally involves disposing a substrate material to be coated in a vacuum chamber. A vaporized initiator and one or more vaporized monomers are then introduced into the chamber. As the monomers are introduced, polymerization occurs on the surface of the substrate material, forming a substantially uniform coating.

In the context of IPG setscrews, the use of vapor deposition provides several significant advantages over conventional manual application of medical adhesive solutions. Regarding initial application, in contrast to the manual application of medical adhesive solutions, vapor deposition enables simultaneous coating of multiple setscrews by placing multiple setscrews in the vacuum chamber and adjusting the quantity of initiator and monomers, accordingly. Vapor deposition polymers, such as parylene, also do not generally require the lengthy curing process associated with medical adhesive solutions. Once applied, the vapor-deposited coating is also not subject to the flowing behavior that occurs with conventional medical adhesive solutions. As a result, the problems associated with local buildups and intrusion of the coating into unwanted areas, such as the setscrew socket, are minimized or precluded with proper masking of the setscrew.

Another advantage of the vapor deposition process is that the thickness of the resulting coating can be controlled by modifying the quantity of initiator and monomer that is vaporized and introduced into the vacuum chamber. In the context of IPG setscrews, control of the thickness of the vapor-deposited coating may be used to control and tune the degree of thread locking provided by the coating. So, for example, a thicker coating may be used to ensure a tighter fit between the setscrew and the header, thereby reducing the likelihood of the setscrew loosening over time. Increasing the thickness of the vapor-deposited coating may also help to accommodate wider manufacturing tolerances of the setscrew and the threaded hole of the header.

The setscrews, IPGs including such setscrews, and corresponding methods of assembly disclosed herein are advantageous for at least the foregoing reasons. Before beginning a detailed discussion of the setscrews and corresponding IPGs, a general discussion is first given regarding features of a common lead connector end at the proximal end of an implantable medical lead followed by a general discussion of the features of an IPG. While the following discussion of the implantable electronic device is given in the context on an IPG, it can be readily understood by those of skill in the art that the discussion is applicable to other electrotherapy devices for the pertinent aspects of this disclosure.

A. Overview of Lead Connector End and IPG

Figure 1:
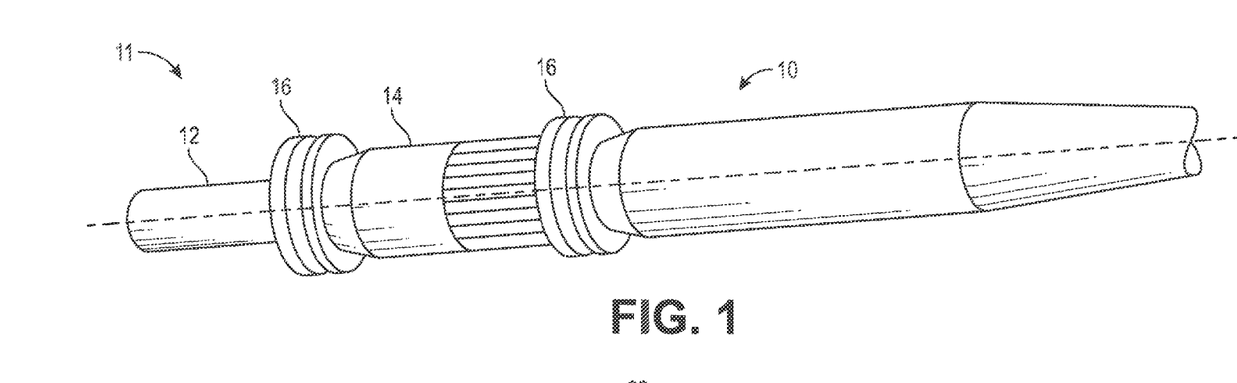
FIG. 1 is an isometric view of a proximal end portion (i.e., lead connector end) of a transvenous bipolar pacing lead.

FIG. 1 shows a proximal end portion 10 of a transvenous, bipolar pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads have proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consist of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, including a pair of coaxial spaced-apart electrical terminals including a tip terminal 12 and a ring terminal 14. The tip terminal 12 is electrically connected via of the inner conductor coil to the tip electrode at the distal end of the lead, while the ring terminal 14 is electrically connected to the anodal ring electrode via of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
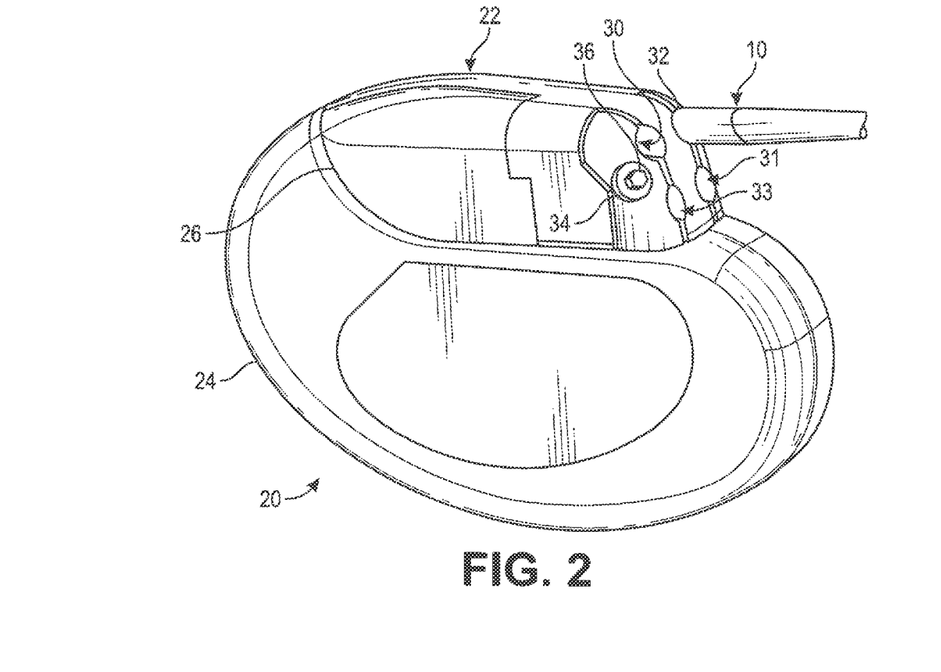
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted respectively in FIGS. 3, 4A and 4B discussed below. The IPG 20 includes a hermetically sealed housing 24, which is also known as a can or casing. The housing 24 encloses the electronic components of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads. One or more setscrews 36 may be threadedly received in respective setscrew bores 34 to secure the proximal end portion 10 of the lead in the header connector assembly 22, as discussed in greater detail below.

Figure 3:
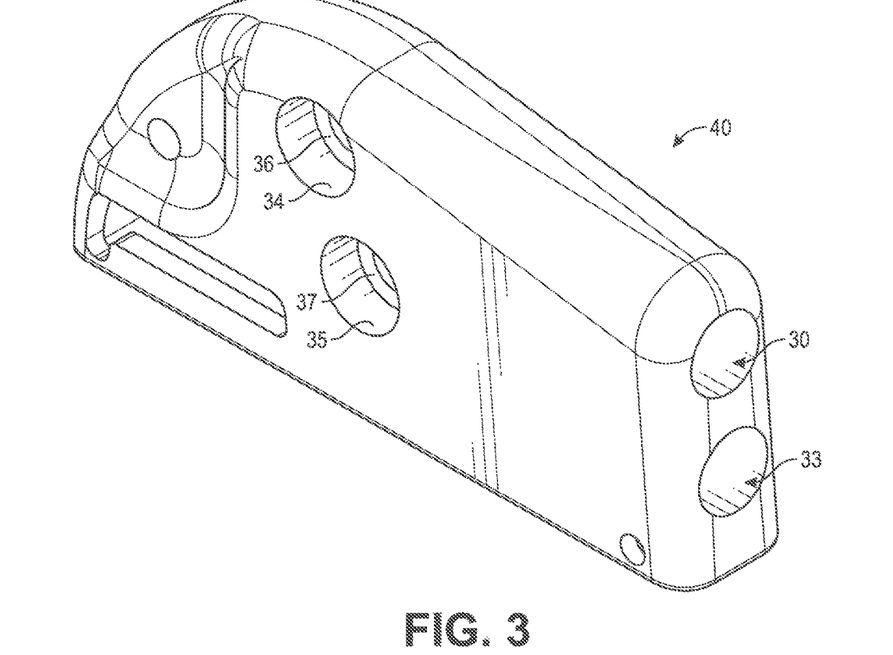
FIG. 3 is an isometric view of a representative header.
Figure 4A:
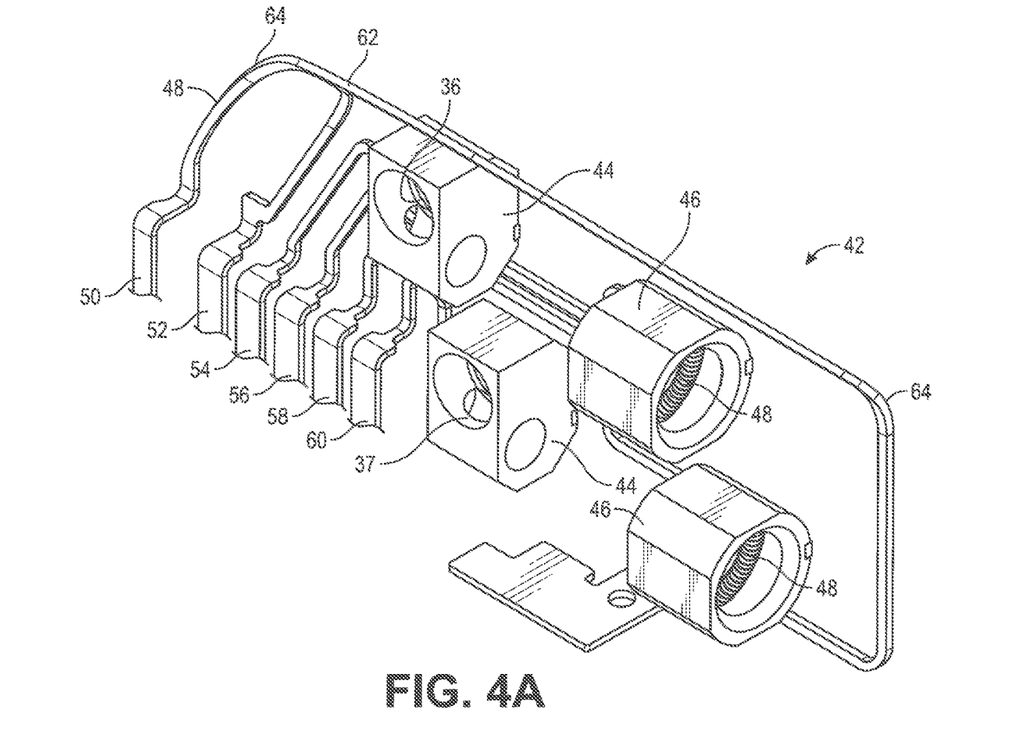
FIGS. 4A and 4B are opposite isometric views of a representative connector assembly used with the header of FIG. 3 to form a header connector assembly.
Figure 4B:
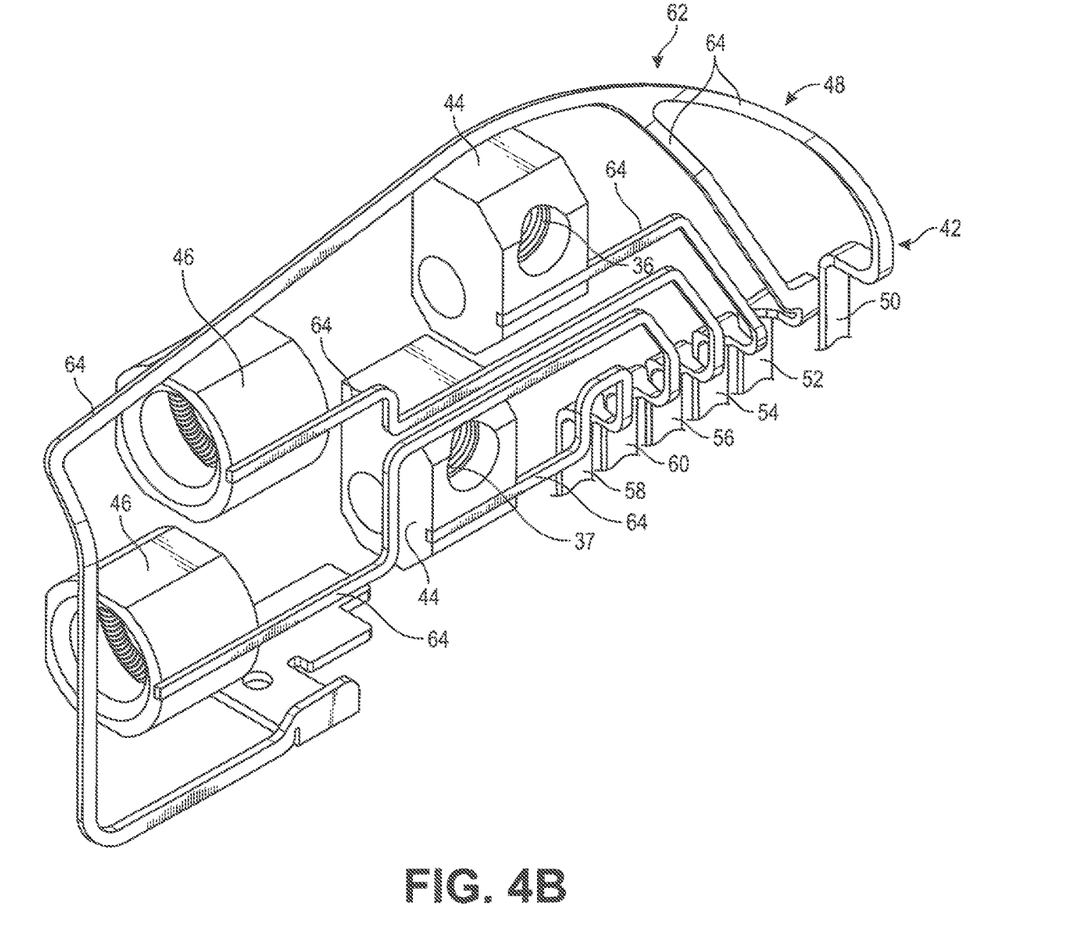

FIG. 3 is an isometric view of a representative header 40, and FIGS. 4A and 4B are opposite isometric views of a representative connector assembly 42. Unlike the header connector assembly 22 of FIG. 2, the header 40 of FIG. 3 only has a single pair of receptacles 30 and 33. However, in other embodiments, the header 40 of FIG. 3 may have two or more pairs of receptacles similar to the embodiment of FIG. 2.

Each receptacle 30, 33 is adapted to receive a proximal end of a lead, such as the proximal end portion 10 illustrated in FIG. 1. As shown in FIG. 3, the header 40 further defines a pair of setscrew bores 34, 35 corresponding to the receptacles 30, 33, respectively. Corresponding setscrews 36, 37 are disposed within the setscrew holes 34, 35 such that when proximal lead ends are fully inserted into the receptacles 30, 33, the setscrews 36, 37 may be tightened to retain the proximal lead ends within the header 40.

As illustrated in FIGS. 4A and 4B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1-4B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIGS. 4A and 4B is of an IS-1 configuration, other configurations (e.g., IS-4, etc.) are used in other embodiments. While the connector assembly 42 of FIGS. 4A and 4B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have a four pairs of blocks 44, 46.

As shown in FIGS. 4A and 4B, the connector assembly 42 also includes a host of electrically conductive components including an antenna 48, a an RF anchor tab 50, an RF pin tab 52, an A-tip tab 54, an A-ring tab 56, an RV-ring tab 58, an RV-tip tab 60, and a ribbon carrier 62 and other conductors 64 that extend between the various tabs and their respective electrical contacts of the connector assembly or other components thereof. In other words, as can be understood from FIGS. 4A and 4B, electrical conductor elements (e.g., wires, traces, or other electrical conductors) 64 extend between the electrical blocks 44, 46 and the respective tabs 50, 52, 54, 56, 58 and 60. Also, such conductor elements 64 may form the antenna 48 and the ribbon carrier 62.

The various tabs are welded to corresponding terminals extending from circuitry of the IPG 20 contained in the housing 24 of the IPG 20 depicted in FIG. 2 when the header connector assembly 22 is joined with the housing 24 to form the IPG 20. The connector assembly 42 is manufactured of materials and via methods known in the industry. The connector assembly 42 is cast in place, injected molded or otherwise installed into the header 40 to form the header connector assembly 22 of FIG. 2, which can be considered a first module that is then attached via a backfill or other process to a second module in the form of the housing 24. In other words, the header connector assembly 22 (i.e., first module) is attached via a backfill or other process to the housing 24 (i.e., the second module) to form the IPG 20.

Figure 5:
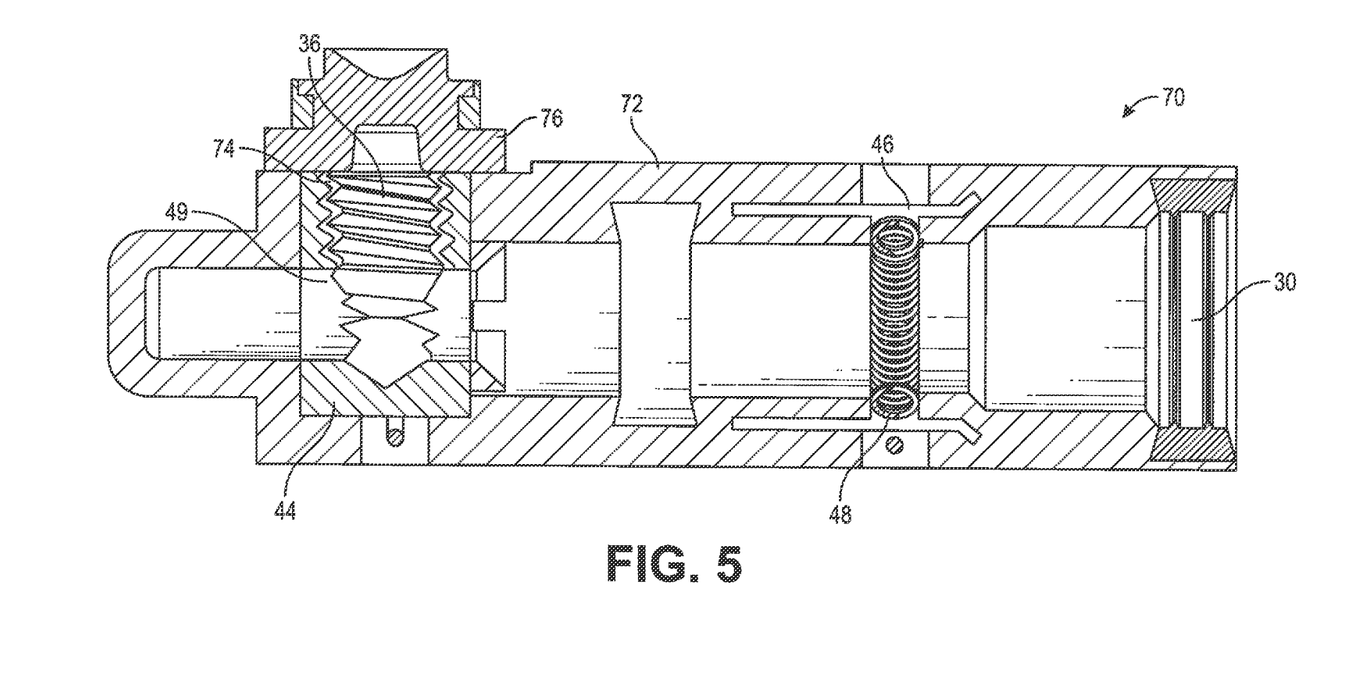
FIG. 5 is a cross sectional view of a representative connector assembly including a coated setscrew.

FIG. 5 is a cross-sectional view of an example connector 70 including a connector housing 72 coupled to each of a tip block 44 and a ring block 46. The connector 70 defines a receptacle 30 into which a proximal end of an implantable lead may be inserted. The ring block 46 includes a spring contact 48 and the tip block 44 includes a compression contact 49 that contact corresponding contacts of the proximal end of the implantable lead when the proximal end is fully inserted into the receptacle 30. The connector housing 72 defines a screw bore 74 adjacent the compression contact 49 into which a setscrew 36 is disposed. Accordingly, after full insertion of the proximal end of the lead into the receptacle 30, the setscrew 36 may be tightened to apply pressure to the compression contact 49 to retain the proximal end within the connector 70.

As illustrated in FIG. 5, the setscrew bore 74 may be covered by a septum 76 that extends through the housing of the IPG. The septum 76 provides a seal or otherwise isolates the setscrew 36 and the setscrew bore 74 from the surrounding tissue when the IPG is implanted within a patient and, as a result, prevents bodily fluids from entering into the connector 70 where such fluids may interfere or disrupt the connection between the contacts 48, 49 of the connector 70 and corresponding contacts of the implantable lead. The septum 76 generally permits insertion of a tool into the setscrew bore 74 to enable adjustment of the setscrew 36 while still maintaining the seal/isolation between the setscrew bore 74 and the surrounding tissue.

B. Thermoplastic-Conductor Subassemblies and Methods of Manufacture and Use

Figure 6A:
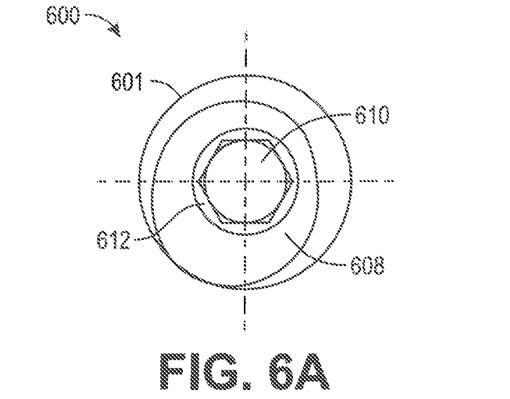
FIG. 6A is a top plan view of an uncoated setscrew.
Figure 6B:
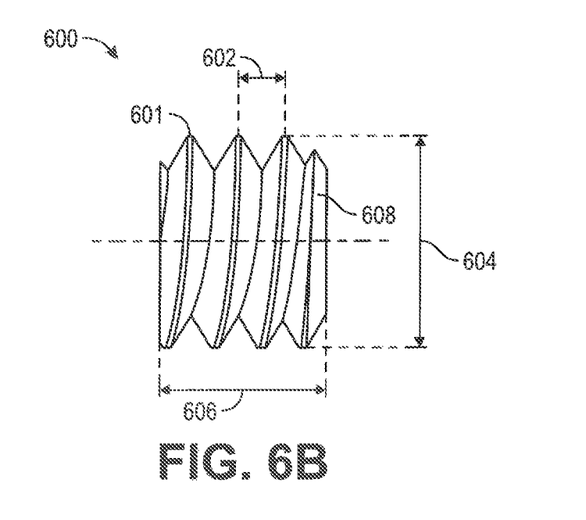
FIG. 6B is a side plan view of the uncoated setscrew of FIG. 6A.
Figure 6C:
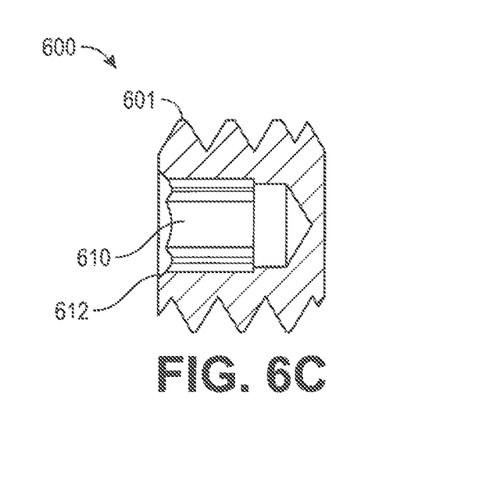
FIG. 6C is a cross-sectional side view of the uncoated setscrew of FIG. 6A.

FIGS. 6A-6C are schematic illustrations of an example setscrew 600 in accordance with the present disclosure in an uncoated state. More specifically, FIG. 6A is a top plan view of the setscrew 600, FIG. 6B is a side plan view of the setscrew 600 and FIG. 6C is a cross-sectional side view of the setscrew 600. The setscrew 600 may be formed from various biocompatible materials. For example, in one implementation, the setscrew 600 may be formed from titanium (such as, without limitation, any of grade 1 to grade 5 titanium) or stainless steel (such as, without limitation, any of 300 series, 400 series, 17-4, and 18-8 stainless steels). The setscrew 600 may also be subjected to a passivation treatment, such as anodization, or similar anti-corrosion treatment.

The size and dimensions of the setscrew 600 may vary based on the specific dimensions of the header into which the setscrew 600 is to be inserted and the lead to be retained by the setscrew 600. However, in certain implementations, the setscrew 600 may include one or more threads, such as a thread 601, having a pitch 602 (shown in FIG. 6B) from and including 0.0125 inches to and including 0.222 inches and a pitch diameter 604 (shown in FIG. 6B) from and including 0.06 inches to and including 2.0 inches. The thread 601 may conform to a standard thread size. For example, in one implementation, the thread 601 may be a #2-56 UNC-2A thread. The setscrew 600 may also have an overall length 606 (shown in FIG. 6B) from and including 0.05 inches to and including 2.0 inches.

The setscrew 600 generally includes a setscrew body 608 defining a socket 610. The socket 610 may vary in shape and dimensions to receive tools of varying different shapes and sizes. The setscrew 600, for example, includes a hexagonal socket 610 into which a hexagonal tool may be inserted to rotate the setscrew 600 within a header. In certain implementations, the socket 610 may include a chamfered opening 612 to guide insertion of the tool into the socket 610.

Figure 7A:
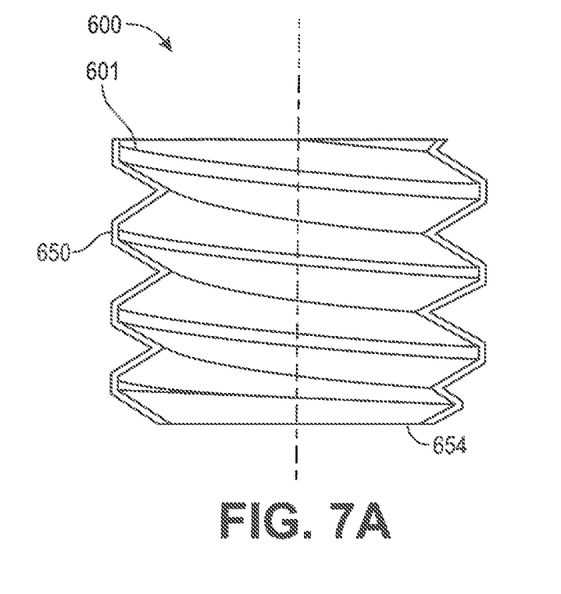
FIG. 7A is a side plane view of a coated setscrew.
Figure 7B:
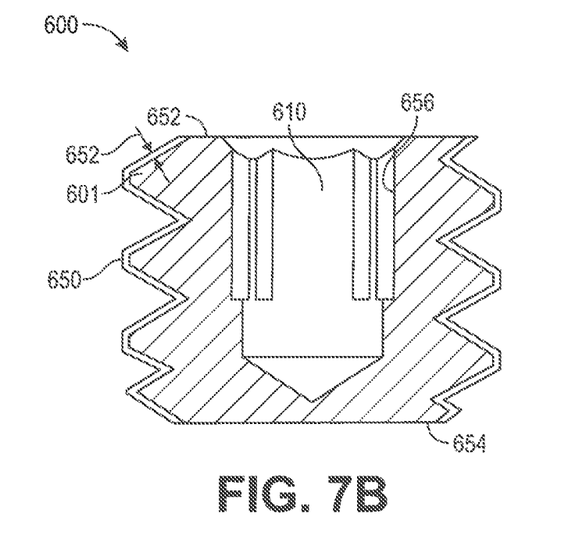
FIG. 7B is a cross-sectional side view of the coated setscrew of FIG. 7A.

FIGS. 7A and 7B are schematic illustrations of the setscrew 600 in a coated state. More specifically, FIG. 7A is a side plan view of the setscrew 600 in a coated state and FIG. 7B is a cross-sectional side view of the setscrew 600 in a coated state.

As shown in FIGS. 7A and 7B, the setscrew 600 includes a coating 650 applied on the thread 601 using a vapor deposition process. In certain implementations, the coating 650 is a poly(p-xylene) polymer, such as parylene. The coating 650 generally extends over at least a portion of the setscrew 600 and, where applied, has a substantially uniform coating thickness 652 (shown in FIG. 7B) as a result of the vapor deposition process. In certain implementations, for example, the coating thickness 652 may be from and including 0.0001 inches to and including 0.005 inches.

Notably, the coating thickness 652 may be purposefully varied to modify the degree of thread locking of the setscrew 600. More specifically, by varying the coating thickness 652 the degree of thread locking and the amount of torque required to screw or unscrew the setscrew 600 may be modified until a desired balance between thread lock and torque required to rotate the screw are achieved. The specific coating thickness 652 required to achieve desired torque and thread locking characteristics for a given setscrew may vary based on, among other things, the geometry of the setscrew and the geometry of the screw bore into which the setscrew is inserted. However, in certain implementations, the coating thickness 652 may be selected such that the torque required to rotate the setscrew 600 is from and including 0.20 ounce-inches to and including 2.0 ounce-inches.

Various surfaces of the setscrew 600 may remain uncoated following the vapor-deposition process. For example, as shown in FIG. 7B, the setscrew 600 includes a top surface 652, a bottom surface 654 and a socket wall 656, each of which is uncoated. To prevent coating, such surfaces may be masked or otherwise covered prior to application of the coating. In certain implementations, for example, a temporary masking coating or material may be disposed on surfaces of the setscrew 600 which are not to receive the vapor-deposited coating. The setscrew 600 may also be disposed on a support fixture or otherwise disposed within the vacuum chamber such that surfaces of the setscrew 600 that are not to be coated are made to abut or otherwise be covered by structural elements of the support fixture or the vacuum chamber. For example, the setscrew 600 may be supported on a fixture having posts shaped to be inserted within the socket 610.

Figure 8:
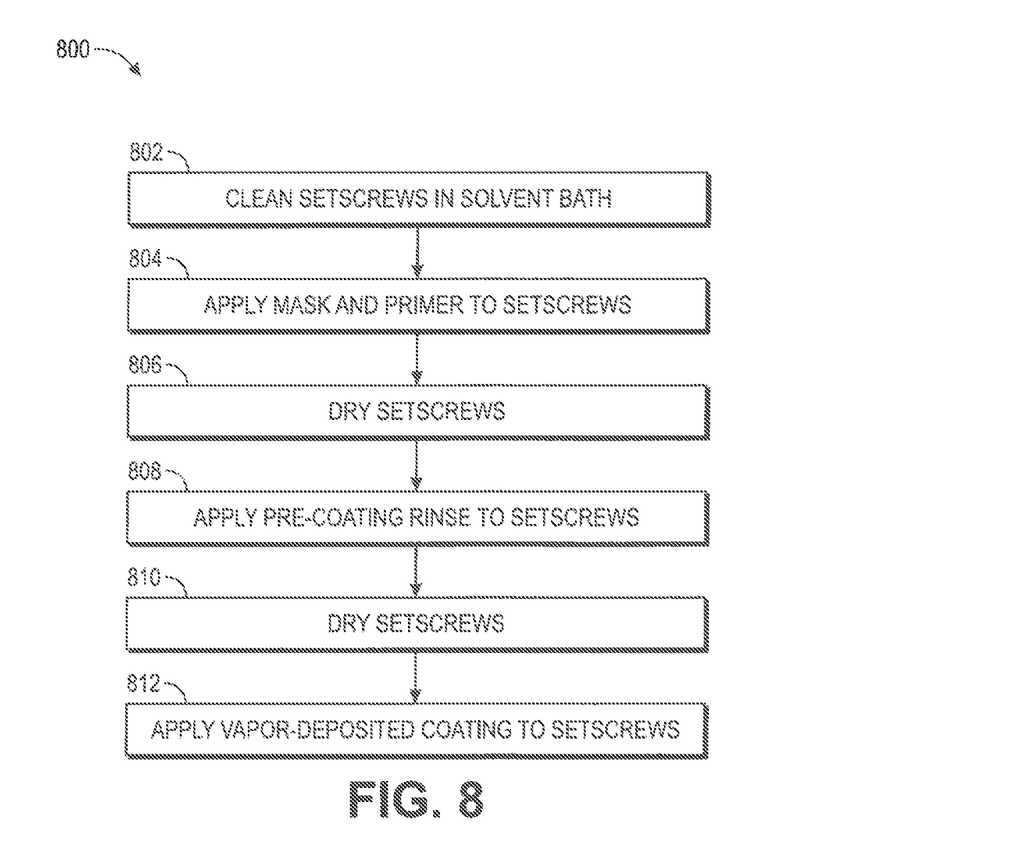
FIG. 8 is a flow chart illustrating a method of applying a vapor-deposited coating to a setscrew.

FIG. 8 is an example method 800 of preparing and coating setscrews in accordance with the present disclosure. The method 800 generally involves cleaning and preparing uncoated setscrews for a final application of a vapor-deposited coating, such as parylene. Although referred to herein as being "uncoated", setscrews that may be subjected to the method 900 may receive a prior coating or surface treatment, such as an anodization or similar passivation treatment, prior to undergoing the method 900.

At operations 802-806 are directed to priming setscrews prior to application of a vapor-deposited coating. At operation 802, an initial cleaning operation is performed by submerging the setscrews into an alcohol-based bath. In certain implementations, for example, the bath may be an ion exchange bath in a 75%-25% mixture of a solvent, such as isopropyl alcohol (IPA) and process water.

At operation 804, the setscrews may be primed to improve adhesion of the vapor-deposited coating to the underlying setscrew substrate. In certain implementations, priming may be performed by submerging the setscrews in a priming bath including an adhesion promoter, such as silane.

The priming operation 804 may also include applying one or more masks to portions of the setscrews to prevent the masked portions from being primed and subsequently coated with the vapor-deposited coating. Masking may be performed by applying, among other things, one or more of masking dots, tape, and contact pads to the setscrews or coating the setscrews in a masking solution, such as liquid latex. In certain implementations, the masking materials are peelable or soluble for ease of their removal after applying the vapor-deposited coating.

At operation 806, the setscrews are dried using one or more drying techniques including, but not limited to blow drying, baking in a low temperature oven (such as a vacuum oven), and air drying. For example, in one implementation, the setscrews may be blown dry with filtered air at 50 psi or greater and subsequently placed in a vacuum oven set at fifty degrees Celsius for six or more minutes. The setscrews may then be cooled and air dried at room temperature for an additional fifteen minutes.

In certain implementations, the process of priming the setscrews may occur separately from the process of applying the vapor-deposited coating. Accordingly, at operation 808, the setscrews may be subjected to a second cleaning operation. For example, one or more isopropyl alcohol or similar rinses may be applied to the setscrews for a predetermined time.

At operation 808, the setscrews may again be dried via one or more of the previously discussed drying techniques. Because the quality of the vapor-deposited coating may be compromised by the presence of moisture on the substrate material being coated, drying operation 808 may be more extensive than the prior drying operation 806 following priming. For example, in addition to a blow drying operation, the setscrews may be subjected to the low temperature vacuum oven for a time period exceeding one hour.

At operation 810, the vapor-deposited coating is applied to the setscrews. The process of coating the setscrews using the vapor-deposited coating generally involves first placing the setscrews into a coating chamber, which is generally maintained at a stable vacuum. Vaporized monomer is then introduced into the coating chamber. While in the coating chamber, molecules of the vaporized monomer undergo polymerization and deposit onto the setscrew substrate, forming the vapor-deposited coating. The vaporized monomer is obtained by first sublimating a solid dimer. The sublimated dimer is then passed into a furnace and heated. The heating process cleaves the dimer molecules through pyrolysis into their corresponding monomer components, thereby producing the monomer vapor that is then introduced into the coating chamber.

The thickness of the vapor-deposited coating applied to the setscrews is generally a function of the amount of dimer used to obtain the vaporized monomer and the exposed surface area within the vacuum chamber to which the vapor-deposition coating may adhere. Accordingly, the amount of dimer used to coat one or more screws may be calculated based on the known geometry of the coating chamber, the screws, and any additional items that may be disposed within the coating chamber. Similarly, increasing the thickness of the vapor-deposited coating generally involves proportionally increasing the quantity of dimer that is vaporized and introduced into the coating chamber.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable electronic device for use with an implantable medical lead, the implantable medical lead including a proximal lead end, the implantable electronic device comprising:
   a housing;
   a header connector assembly coupled to the housing and defining a threaded setscrew bore, the header connector assembly comprising a connector assembly adjacent the threaded setscrew bore, the connector assembly adapted to receive the proximal lead end of the implantable medical lead; and
   a setscrew threadedly movable within the threaded setscrew bore to retain the proximal lead end within the connector assembly, the setscrew comprising:
      an anodized threaded body and a vapor-deposited coating disposed on a threaded portion of the anodized threaded body, the anodized threaded body defining a socket that is not coated by the vapor-deposited coating and that extends into the anodized threaded body, the socket shaped to receive a tool adapted to rotate the setscrew within the threaded setscrew bore.

2. The implantable electronic device of claim 1, wherein the vapor-deposited coating is a poly(p-xylelene) polymer coating.

3. The implantable electronic device of claim 2, wherein the vapor-deposited coating is a parylene coating.

4. The implantable electronic device of claim 1, wherein the vapor-deposited coating has a thickness from and including 0.0001 inches to and including 0.005 inches.

5. The implantable electronic device of claim 1, wherein the setscrew is formed from a substrate material selected from a group of substrate materials including titanium and stainless steel.

6. The implantable electronic device of claim 1, wherein the anodized threaded body comprises a thread having a pitch from and including 0.0125 inches to and including 0.2222 inches and a pitch diameter from and including 0.060 inches in to and including 2.00 inches.

7. The implantable electronic device of claim 1, wherein the torque required to rotate the setscrew within the threaded setscrew bore is from and including 0.2 ounce-inches to and including 2.0 ounce-inches.

8. A method of manufacturing an implantable electronic device including a header that further includes a connector assembly and a threaded setscrew bore adjacent the connector assembly, the method comprising:
producing a coated setscrew by applying a vapor-deposited coating to threads of an anodized setscrew substrate, the anodized setscrew substrate including a socket that is not coated by the vapor-deposited coating and that extends into the anodized setscrew substrate, the socket shaped to receive a tool adapted to rotate the setscrew within the threaded setscrew bore; and
at least one of providing the coated setscrew with the implantable electronic device or threadedly engaging the coated setscrew within the threaded setscrew bore.

9. The method of claim 8, wherein the vapor-deposited coating is a poly(p-xylelene) polymer.

10. The method of claim 9, wherein the vapor-deposited coating is parylene.

11. The method of claim 8, wherein the vapor-deposited coating is has a thickness from and including 0.0002 inches to and including 0.005 inches.

12. The method of claim 8 further comprising applying a primer to the anodized setscrew substrate before applying the vapor-deposited coating.

13. The method of claim 12, wherein the primer includes silane.

14. The method of claim 8 further comprising masking a portion of the anodized setscrew substrate such that the vapor-deposited coating is not applied to the masked portion of the anodized setscrew substrate.

15. The method of claim 14, wherein masking the portion of the setscrew comprises applying at least one of a masking dot, tape, a contact pad, and a masking solution to the portion of the setscrew.

16. The method of claim 8, wherein the method further comprises supporting the setscrew on a fixture shaped to be inserted into the socket such that the fixture prevents application of the vapor-deposited coating to the socket.

* * * * *